US010188555B2

(12) United States Patent
Vitaris et al.

(10) Patent No.: US 10,188,555 B2
(45) Date of Patent: *Jan. 29, 2019

(54) SHEAR RESISTANT WOUND DRESSING FOR USE IN VACUUM WOUND THERAPY

(71) Applicant: Smith & Nephew, Inc., Memphis, TN (US)

(72) Inventors: Ronald F. Vitaris, Worcester, MA (US); Bethany A. Vitaris, Worcester, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/192,675

(22) Filed: Jun. 24, 2016

(65) Prior Publication Data

US 2016/0317357 A1    Nov. 3, 2016

Related U.S. Application Data

(63) Continuation of application No. 14/948,024, filed on Nov. 20, 2015, now Pat. No. 9,375,353, which is a
(Continued)

(51) Int. Cl.
*A61M 1/00* (2006.01)
*A61F 13/00* (2006.01)
(Continued)

(52) U.S. Cl.
CPC .. *A61F 13/00068* (2013.01); *A61F 13/00029* (2013.01); *A61F 13/00046* (2013.01);
(Continued)

(58) Field of Classification Search
CPC ......... A61M 1/00; A61M 27/00; A61F 13/00; A61F 13/02
See application file for complete search history.

(56) References Cited

U.S. PATENT DOCUMENTS 3,367,332 A    2/1968   Groves
3,486,504 A   12/1969   Austin, Jr.
(Continued)

FOREIGN PATENT DOCUMENTS

DE    34 43 101    5/1986
DE    4 012 232   10/1991
(Continued)

OTHER PUBLICATIONS

US 6,216,701, 04/2001, Heaton et al. (withdrawn)
(Continued)

*Primary Examiner* — Tatyana Zalukaeva
*Assistant Examiner* — Ilya Treyger
(74) *Attorney, Agent, or Firm* — Knobbe, Martens, Olson & Bear, LLP (57) ABSTRACT

A cover layer for a vacuum wound therapy dressing includes a backing layer formed from a flexible polymeric membrane and an adhesive layer for affixing the backing layer over a wound bed to provide a substantially fluid-tight seal around a perimeter of the wound bed. The cover layer is reinforced with a reinforcement layer extending to a peripheral region of the backing layer to distribute forces associated with evacuating a reservoir, as defined by or within the cover, to stimulate healing of the wound bed.

20 Claims, 7 Drawing Sheets

Related U.S. Application Data continuation of application No. 12/402,840, filed on Mar. 12, 2009, now Pat. No. 9,199,012.

(60) Provisional application No. 61/036,275, filed on Mar. 13, 2008.

(51) Int. Cl.
*A61F 13/02* (2006.01)
*A61M 27/00* (2006.01)

(52) U.S. Cl.
CPC ....... *A61F 13/0216* (2013.01); *A61M 1/0049* (2013.01); *A61M 1/0052* (2014.02); *A61M 1/0088* (2013.01); *A61F 2013/0054* (2013.01); *A61F 2013/00174* (2013.01); *A61F 2013/00536* (2013.01); *A61M 2205/7545* (2013.01)

(56) References Cited

U.S. PATENT DOCUMENTS

| | | |
|---|---|---|
| 3,568,675 A | 3/1971 | Harvey |
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 3,972,328 A | 8/1976 | Chen |
| 4,029,598 A | 6/1977 | Neisius et al. |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,228,798 A * | 10/1980 | Deaton ............... A61M 1/0052 604/320 |
| 4,266,545 A | 5/1981 | Moss |
| 4,382,441 A | 5/1983 | Svedman |
| 4,524,064 A | 6/1985 | Nambu |
| 4,605,399 A | 8/1986 | Weston et al. |
| 4,655,754 A | 4/1987 | Richmond et al. |
| 4,743,232 A | 5/1988 | Kruger |
| 4,813,942 A | 3/1989 | Alvarez |
| 4,826,494 A | 5/1989 | Richmond et al. |
| 4,846,164 A | 7/1989 | Martz |
| 4,969,880 A | 11/1990 | Zamierowski |
| 4,990,137 A | 2/1991 | Graham |
| 4,997,438 A | 3/1991 | Nipper |
| 5,056,510 A | 10/1991 | Gilman |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,181,905 A | 1/1993 | Flam |
| 5,195,977 A | 3/1993 | Pollitt |
| 5,234,419 A | 8/1993 | Bryant et al. |
| 5,238,732 A | 8/1993 | Krishnan |
| 5,261,893 A | 11/1993 | Zamierowski |
| 5,263,922 A | 11/1993 | Sova et al. |
| D364,679 S | 11/1995 | Heaton et al. |
| 5,484,427 A | 1/1996 | Gibbons |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,599,289 A | 2/1997 | Castellana |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,707,499 A | 1/1998 | Joshi et al. |
| 5,733,305 A | 3/1998 | Fleischmann |
| 5,759,570 A | 6/1998 | Arnold |
| 5,795,584 A | 8/1998 | Totakura et al. |
| 5,840,049 A | 11/1998 | Tumey et al. |
| 5,897,541 A | 4/1999 | Uitenbrock et al. |
| 5,911,222 A | 6/1999 | Lawrence et al. |
| 5,944,703 A | 8/1999 | Dixon et al. |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| D434,150 S | 11/2000 | Turney et al. |
| 6,142,982 A * | 11/2000 | Hunt ................... A61M 1/0052 604/313 |
| 6,168,800 B1 | 1/2001 | Dobos et al. |
| 6,174,306 B1 | 1/2001 | Fleischmann |
| 6,203,563 B1 | 3/2001 | Fernandez |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,362,390 B1 | 3/2002 | Carlucci et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| 6,520,982 B1 | 2/2003 | Boynton et al. |
| 6,553,998 B2 | 4/2003 | Heaton et al. |
| D475,134 S | 5/2003 | Randolph |
| 6,557,704 B1 | 5/2003 | Randolph |
| 6,586,653 B2 | 7/2003 | Graeme, III et al. |
| D469,175 S | 8/2003 | Hall et al. |
| D469,176 S | 8/2003 | Hall et al. |
| D478,659 S | 8/2003 | Hall et al. |
| 6,607,495 B1 | 8/2003 | Skalak |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,719,742 B1 | 4/2004 | McCormack et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hanningan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |

(56) References Cited

U.S. PATENT DOCUMENTS

| | | |
|---|---|---|
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,429,687 B2 * | 9/2008 | Kauth .................. A61F 13/143 128/887 |
| 7,429,689 B2 | 9/2008 | Chen et al. |
| 7,438,705 B2 | 10/2008 | Karpowicz et al. |
| 7,485,112 B2 | 2/2009 | Karpowicz et al. |
| 7,511,187 B2 | 3/2009 | Kelly |
| 7,569,742 B2 | 8/2009 | Haggstrom et al. |
| 7,605,298 B2 | 10/2009 | Bechert et al. |
| 7,615,036 B2 | 11/2009 | Joshi et al. |
| 7,622,629 B2 | 11/2009 | Aail |
| 7,625,362 B2 | 12/2009 | Boehringer et al. |
| 7,670,323 B2 | 3/2010 | Hunt et al. |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,722,582 B2 | 5/2010 | Lina et al. |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,896,856 B2 | 3/2011 | Petrosenko et al. |
| 7,909,805 B2 | 3/2011 | Weston |
| 7,910,791 B2 | 3/2011 | Coffey |
| 7,922,703 B2 | 4/2011 | Riesinger |
| 7,942,866 B2 | 5/2011 | Radl et al. |
| 7,959,624 B2 | 6/2011 | Riesinger |
| 7,964,766 B2 | 6/2011 | Blott et al. |
| 7,976,519 B2 | 7/2011 | Bubb et al. |
| 8,007,257 B2 | 8/2011 | Heaton et al. |
| 8,062,272 B2 | 11/2011 | Weston |
| 8,062,331 B2 | 11/2011 | Zamierowski |
| 8,080,702 B2 | 12/2011 | Blott et al. |
| 8,083,712 B2 | 12/2011 | Biggie et al. |
| 8,092,436 B2 | 1/2012 | Christensen |
| 8,118,794 B2 | 2/2012 | Weston |
| 8,152,785 B2 | 4/2012 | Vitaris |
| 8,162,907 B2 | 4/2012 | Heagle |
| 8,207,392 B2 | 6/2012 | Haggstrom et al. |
| 8,235,972 B2 | 8/2012 | Adahan |
| 8,241,261 B2 | 8/2012 | Randolph et al. |
| 8,267,908 B2 | 9/2012 | Coulthard |
| 8,282,611 B2 | 10/2012 | Weston |
| 8,298,200 B2 | 10/2012 | Vess et al. |
| 8,303,552 B2 | 11/2012 | Weston |
| 8,372,049 B2 | 2/2013 | Jaeb et al. |
| 8,372,050 B2 | 2/2013 | Jaeb et al. |
| 8,425,478 B2 | 4/2013 | Olson |
| 8,444,612 B2 | 5/2013 | Patel et al. |
| 8,460,255 B2 | 6/2013 | Joshi et al. |
| 8,535,283 B2 | 9/2013 | Heaton et al. |
| 8,545,466 B2 | 10/2013 | Andresen et al. |
| 8,556,871 B2 | 10/2013 | Mormino et al. |
| 8,568,386 B2 | 10/2013 | Malhi |
| 8,569,566 B2 | 10/2013 | Blott et al. |
| 8,628,505 B2 | 1/2014 | Weston |
| 8,641,691 B2 | 2/2014 | Fink et al. |
| 8,663,198 B2 | 3/2014 | Buan et al. |
| 8,679,079 B2 | 3/2014 | Heaton et al. |
| 8,715,256 B2 | 5/2014 | Greener |
| 8,747,376 B2 | 6/2014 | Locke et al. |
| 8,764,732 B2 | 7/2014 | Hartwell |
| 8,795,243 B2 | 8/2014 | Weston |
| 8,808,274 B2 | 8/2014 | Hartwell |
| 8,829,263 B2 | 9/2014 | Haggstrom et al. |
| 8,834,451 B2 | 9/2014 | Haggstrom et al. |
| 8,834,452 B2 | 9/2014 | Hudspeth et al. |
| 8,864,748 B2 | 10/2014 | Coulthard et al. |
| 8,915,895 B2 | 12/2014 | Jaeb et al. |
| 8,956,336 B2 | 2/2015 | Haggstrom et al. |
| 9,061,095 B2 | 6/2015 | Adie et al. |
| 9,127,665 B2 | 9/2015 | Locke et al. |
| 9,168,330 B2 | 10/2015 | Joshi et al. |
| 9,199,012 B2 | 12/2015 | Vitaris et al. |
| 9,220,822 B2 | 12/2015 | Hartwell et al. |
| 9,283,118 B2 | 3/2016 | Locke et al. |
| 9,302,033 B2 | 4/2016 | Riesinger |
| 9,375,521 B2 | 6/2016 | Hudspeth et al. |
| 9,381,283 B2 | 7/2016 | Adams et al. |
| 9,446,178 B2 | 9/2016 | Blott et al. |
| 9,452,248 B2 | 9/2016 | Blott et al. |
| 9,669,138 B2 | 6/2017 | Joshi et al. |
| 9,795,725 B2 | 10/2017 | Joshi et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0110672 A1 | 8/2002 | Muratore-Pallatino et al. |
| 2002/0143286 A1 | 10/2002 | Tumey |
| 2002/0151836 A1 | 10/2002 | Burden |
| 2003/0093041 A1 | 5/2003 | Risk, Jr. et al. |
| 2003/0114818 A1 | 6/2003 | Benecke et al. |
| 2003/0180341 A1 | 9/2003 | Gooch et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0057855 A1 | 3/2004 | Gerlach et al. |
| 2004/0064132 A1 | 4/2004 | Boehringer et al. |
| 2004/0093026 A1 | 5/2004 | Weidenhagen et al. |
| 2004/0122434 A1 | 6/2004 | Argenta et al. |
| 2004/0193218 A1 | 9/2004 | Butler |
| 2004/0241213 A1 | 12/2004 | Bray |
| 2004/0243042 A1 | 12/2004 | Lipman |
| 2004/0243073 A1 | 12/2004 | Lockwood et al. |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0101940 A1 | 5/2005 | Radl et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0261643 A1 | 11/2005 | Bybordi et al. |
| 2006/0003604 A1 | 1/2006 | Angerpointner |
| 2006/0009744 A1 | 1/2006 | Erdman et al. |
| 2006/0015087 A1 | 1/2006 | Risk, Jr. et al. |
| 2006/0020234 A1 | 1/2006 | Chou et al. |
| 2006/0039742 A1 | 2/2006 | Cable, Jr. et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0127462 A1 | 6/2006 | Canada et al. |
| 2006/0149170 A1 | 7/2006 | Boynton et al. |
| 2006/0155260 A1 | 7/2006 | Blott et al. |
| 2007/0005028 A1 | 1/2007 | Risk, Jr. et al. |
| 2007/0014837 A1 | 1/2007 | Johnson et al. |
| 2007/0021697 A1 | 1/2007 | Ginther et al. |

(56) References Cited

U.S. PATENT DOCUMENTS

| | | |
|---|---|---|
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0040454 A1 | 2/2007 | Freudenberger et al. |
| 2007/0055209 A1 | 3/2007 | Patel et al. |
| 2007/0100308 A1 | 5/2007 | Miyairi |
| 2007/0179460 A1 | 8/2007 | Adahan |
| 2007/0225663 A1 | 9/2007 | Watt et al. |
| 2007/0264520 A1 | 11/2007 | Wood et al. |
| 2007/0265586 A1 | 11/2007 | Joshi et al. |
| 2007/0270737 A1 | 11/2007 | Jennings et al. |
| 2007/0293830 A1 | 12/2007 | Martin |
| 2008/0031748 A1 | 2/2008 | Ihle et al. |
| 2008/0071235 A1 | 3/2008 | Locke et al. |
| 2008/0108977 A1 | 5/2008 | Heaton et al. |
| 2008/0132821 A1 | 6/2008 | Propp et al. |
| 2008/0200857 A1 | 8/2008 | Lawhorn |
| 2008/0200905 A1 | 8/2008 | Heaton et al. |
| 2008/0200906 A1 | 8/2008 | Sanders et al. |
| 2008/0208147 A1 | 8/2008 | Argenta et al. |
| 2008/0234641 A1 | 9/2008 | Locke et al. |
| 2008/0306456 A1 | 12/2008 | Riesinger |
| 2009/0069759 A1 | 3/2009 | Blott et al. |
| 2009/0125004 A1 | 5/2009 | Shen et al. |
| 2009/0137973 A1 | 5/2009 | Karpowicz et al. |
| 2009/0157024 A1 | 6/2009 | Song |
| 2009/0204085 A1 | 8/2009 | Biggie et al. |
| 2009/0227969 A1 | 9/2009 | Jaeb et al. |
| 2009/0234306 A1 | 9/2009 | Vitaris |
| 2009/0240185 A1 | 9/2009 | Jaeb et al. |
| 2009/0275922 A1 | 11/2009 | Coulthard et al. |
| 2009/0299251 A1 | 12/2009 | Buan |
| 2009/0299306 A1 | 12/2009 | Buan |
| 2010/0063484 A1 | 3/2010 | Heagle |
| 2010/0125258 A1 | 5/2010 | Coulthard et al. |
| 2010/0256586 A1 | 10/2010 | Bergstrom et al. |
| 2010/0305526 A1 | 12/2010 | Robinson et al. |
| 2010/0318052 A1 | 12/2010 | Ha et al. |
| 2011/0004172 A1 | 1/2011 | Eckstein et al. |
| 2011/0054421 A1 | 3/2011 | Hartwell |
| 2011/0118683 A1 | 5/2011 | Weston |
| 2011/0224631 A1 | 9/2011 | Simmons |
| 2011/0295220 A1 | 12/2011 | Heaton et al. |
| 2012/0041399 A1 | 2/2012 | Blott et al. |
| 2012/0095380 A1 | 4/2012 | Gergeley et al. |
| 2012/0095426 A1 | 4/2012 | Visscher et al. |
| 2012/0203145 A1 | 8/2012 | Nilsson |
| 2013/0066285 A1 | 3/2013 | Locke et al. |
| 2013/0066289 A1 | 3/2013 | Song et al. |
| 2013/0090615 A1 | 4/2013 | Jaeb et al. |
| 2013/0090616 A1 | 4/2013 | Neubauer |
| 2013/0102979 A1 | 4/2013 | Coulthard et al. |
| 2013/0116635 A1 | 5/2013 | Fleischmann |
| 2013/0138054 A1 | 5/2013 | Fleischmann |
| 2013/0144230 A1 | 6/2013 | Wu et al. |
| 2013/0150814 A1 | 6/2013 | Buan |
| 2013/0165878 A1 | 6/2013 | Heagle |
| 2013/0274688 A1 | 10/2013 | Weston |
| 2013/0331822 A1 | 12/2013 | Patel |
| 2013/0338613 A1 | 12/2013 | Haggstrom |
| 2013/0338614 A1 | 12/2013 | Heaton et al. |
| 2014/0100539 A1 | 4/2014 | Coulthard et al. |
| 2014/0114268 A1 | 4/2014 | Auguste et al. |
| 2014/0155849 A1 | 6/2014 | Heaton et al. |
| 2014/0188061 A1 | 7/2014 | Locke et al. |
| 2014/0200535 A1 | 7/2014 | Locke et al. |
| 2014/0228791 A1 | 8/2014 | Hartwell |
| 2014/0236109 A1 | 8/2014 | Greener |
| 2014/0276490 A1 | 9/2014 | Locke et al. |
| 2014/0276491 A1 | 9/2014 | Luckemeyer et al. |
| 2014/0276497 A1 | 9/2014 | Robinson |
| 2014/0309601 A1 | 10/2014 | Hall et al. |
| 2014/0316359 A1 | 10/2014 | Collinson et al. |
| 2015/0032035 A1 | 1/2015 | Banwell et al. |
| 2015/0065965 A1 | 3/2015 | Haggstrom |
| 2015/0209492 A1 | 7/2015 | Blott et al. |
| 2015/0308994 A1 | 10/2015 | Hammond et al. |
| 2016/0074232 A1 | 3/2016 | Vitaris |
| 2016/0081859 A1 | 3/2016 | Hartwell |
| 2016/0144084 A1 | 5/2016 | Collinson et al. |
| 2017/0128642 A1 | 5/2017 | Buan |
| 2017/0181896 A1 | 6/2017 | Hartwell |
| 2017/0181897 A1 | 6/2017 | Hartwell |

FOREIGN PATENT DOCUMENTS

| | | |
|---|---|---|
| DE | 41 11 122 A1 | 4/1993 |
| DE | 295 04 378 U1 | 10/1995 |
| DE | 20 2004 017 052 | 7/2005 |
| EP | 0 020 662 | 7/1984 |
| EP | 0 257 916 | 3/1988 |
| EP | 0 340 018 | 11/1989 |
| EP | 0 358 302 | 3/1990 |
| EP | 0 853 950 | 7/1998 |
| EP | 1 452 156 | 9/2004 |
| EP | 1 476 217 | 11/2004 |
| EP | 1 955 887 | 8/2008 |
| EP | 2 079 507 | 7/2009 |
| EP | 2 252 247 A2 | 11/2010 |
| EP | 2 021 046 | 3/2012 |
| EP | 2 462 908 | 6/2012 |
| EP | 2079507 | 1/2014 |
| EP | 2 711 034 | 3/2014 |
| EP | 2 305 325 | 4/2014 |
| EP | 2 345 437 | 4/2014 |
| EP | 2 687 245 | 9/2014 |
| EP | 2 544 642 | 1/2015 |
| EP | 2 648 668 | 1/2015 |
| EP | 2 836 711 | 2/2015 |
| FR | 1163907 | 10/1958 |
| GB | 1 255 395 | 12/1971 |
| GB | 1 549 756 | 8/1979 |
| GB | 2 195 255 A | 4/1988 |
| GB | 2 235 877 A | 3/1991 |
| SU | 1762940 | 1/1989 |
| WO | WO 1980/01139 | 6/1980 |
| WO | WO 1980/02182 | 10/1980 |
| WO | WO 1983/00742 | 3/1983 |
| WO | WO 1984/01904 | 5/1984 |
| WO | WO 1989/05133 | 6/1989 |
| WO | WO 1990/11795 | 10/1990 |
| WO | WO 1992/19313 | 11/1992 |
| WO | WO 1995/29959 | 11/1995 |
| WO | WO 1996/05873 | 2/1996 |
| WO | WO 1999/39671 | 8/1999 |
| WO | WO 2001/85248 | 11/2001 |
| WO | WO 2002/076379 | 10/2002 |
| WO | WO 2012/143665 | 10/2002 |
| WO | WO 2003/057307 | 7/2003 |
| WO | WO 2003/101508 | 12/2003 |
| WO | WO 2004/077387 | 9/2004 |
| WO | WO 2005/009488 | 2/2005 |
| WO | WO 2005/025447 | 3/2005 |
| WO | WO 2005/123170 | 12/2005 |
| WO | WO 2006/052338 | 5/2006 |
| WO | WO 2006/052839 | 5/2006 |
| WO | WO 2007/143060 | 12/2007 |
| WO | WO 2008/039223 | 4/2008 |
| WO | WO 2009/066105 | 5/2009 |
| WO | WO 2009/111657 | 9/2009 |
| WO | WO 2009/114786 | 9/2009 |
| WO | WO 2009/114790 | 9/2009 |
| WO | WO 2009/124100 | 10/2009 |
| WO | WO 2009/158128 | 12/2009 |
| WO | WO 2009/114786 | 3/2010 |
| WO | WO 2010/142959 | 12/2010 |
| WO | WO 2010/147533 | 12/2010 |
| WO | WO 2011/112724 | 9/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2012/074512 | 6/2012 |

(56) References Cited

FOREIGN PATENT DOCUMENTS

| | | |
|---|---|---|
| WO | WO 2012/041296 | 8/2012 |
| WO | WO 2012/131237 | 10/2012 |
| WO | WO 2012/140378 | 10/2012 |
| WO | WO 2013/010907 | 1/2013 |
| WO | WO 2013/083800 | 6/2013 |
| WO | WO 2013/090810 | 6/2013 |
| WO | WO 2013/149078 | 10/2013 |
| WO | WO 2013/136181 | 11/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/113504 | 6/2014 |
| WO | WO 2014/108476 | 7/2014 |
| WO | WO 2014/113253 | 7/2014 |
| WO | WO 2014/107285 | 9/2014 |
| WO | WO 2014/143488 | 9/2014 |
| WO | WO 2015/022334 | 2/2015 |
| WO | WO 2015/022340 | 2/2015 |

OTHER PUBLICATIONS

US 7,186,244, 03/2007, Hunt et al. (withdrawn)
U.S. Appl. No. 14/259,026, filed Apr. 22, 2014, Hartwell.
U.S. Appl. No. 14/276,983, filed May 13, 2014, Hartwell.
Chardack, et al., "Experimental studies on Synthetic Substitutes for Skin and Their Use in the Treatment of Burns," vol. 155, No. 1 (128-136), 1961.
Fleischmann, "Vacuum Sealing for Treatment of Problematical Wounds", University Surgical Clinic and Polyclinic—Accident Surgery Department, WundForum Spezial-IHW 94.
Kendall ULTEC Hydrocolloid Dressing (4"x4"), product ordering page, web page downloaded Jul. 13, 2014.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Membrane Filters, in 16 pages, from website: http://www.advantecmfs.com/catalog/filt/membrane.pdf#page=11 (date unknown, but believed to be copyright 2001-2011).
Protz, Kerstin: "Modern Wundauflagen unterstutzen Heilungsprozess", Wundversorgung: Indikation and Anwendung, Geriatrie Journal 4/05, pp. 3333-3339.
Stoll, "Energetic Remedies—Cupping: Healing Within a Vacuum," https:I/www.suite101.com/article.cfm/ energetic)remedies/74531, Apr. 13, 2005.
Svedman, "A Dressing Allowing Continuous Treatment of a Biosurface," IRCS Medical Science: Biomedical Technology; Clinical Medicine; Surgery and Transplantation, 7, 221 (1979).
Svedman, "A Dressing System Providing Fluid Supply and Suction Drainage Used for Continuous or Intermittent Irrigation," Annals of Plastic Surgery, vol. 17, No. 2, Aug. 1986 (125-133).
Svedman, "Irrigation Treatment of Leg Ulcers," The Lancet, Sep. 3, 1983 (532-534).
Teder and Svedman et al., "Continuous Wound Irrigation in the Pig," Journal of Investigative Surgery, 1990, vol. 3, pp. 399-407.
Yu A. Davydov, et al., "Bacteriological and Cylological Assessment of Vacuum Therapy of Purulent Wounds", Vestnik Khirurgii, Oct. 1988, (48-52).
Yu A. Davydov, et al., "Concepts for Clinical Biological Management of the Wound Process in the Treatment of Purulent Wounds Using Vacuum Therapy," Vestnik Khirugii, Feb. 1991, 132-135).
Yu A. Davydov, et al., "Vacuum Therapy in the Treatment of Purulent Lactation Mastitis," Russian Journal: Vesnik Khirurgii, Sep. 1986, (66-70).
Communication of a Notice of Opposition re EP 2 254 647 dated Apr. 26, 2016, in 1 page.
Declaration of Nadeem Bridi dated Apr. 14, 2016, in 1 page.
KCI V.A.C. ATS—An Advanced Therapy System for Wound Healing, 2007, in 8 pages.

Notice of Advice of Delivery re EP 2 254 647 dated Dec. 2, 2016, in 2 pages.
Notice of Brief Communication re EP 2 254 647 dated May 10, 2016, in 1 page.
Notice of Brief Communication re EP 2 254 647 dated May 30, 2016, in 5 pages.
Notice of Brief Communication re EP 2 254 647 dated Sep. 30, 2016, in 1 page.
Notice of Further Oppositions to Opponents re EP 2 254 647 dated Jun. 1, 2016, in 2 pages.
Notice of Opposition—Statement of Facts and Evidence re EP 2 254 647 dated Apr. 19, 2016, in 111 pages.
Reply of the Patent Proprietor to the Notice(s) of Opposition re EP 2 254 647 dated Sep. 26, 2016, in 23 pages.
Request for Change of Applicant's Representative re EP 2 254 647 dated May 4, 2016, in 4 pages.
Summons to Attend Oral Proceedings re EP 2 254 647 dated Nov. 28, 2016, in 17 pages.
U.S. Appl. No. 12/402,840, filed Mar. 12, 2009, Shear Resistant Wound Dressing for Use in Vacuum Wound Terapy, U.S. Pat. No. 9,199,012.
U.S. Appl. No. 14/948,024, filed Nov. 20, 215, Shear Resistant Wound Dressing for Use in Vacuum Wound Terapy, 9,375,353.
U.S. Appl. No. 12/402,893, filed Mar. 12, 2009, Vacuum Port for Vacuum Wound Therapy, 8,152,785.
Fleischmann, W. et al., "Vacuum Sealing: Indication, Technique and Results", Emr J Orthop Surg Tramatol (1995) 5:37-40.
International Search Report for PCT/US09/37127 dated Dec. 23, 2009, 7 pages.
Aubrey, D.A., et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Bier, A., Hyperemia as a Therapeutic Agent, Ed. Dr. Gustavus M. Blech, A. Robertson & Co., Chicago 1905.
Arnljots, et al., "Irrigation Treatment in Split-thickness Skin Grafting of Intractable Leg Ulcers," Scand J Plast Reconstr Surg 19: 211-213,1985.
Bucalo et al. "Inhibition of Cell Proliferation by Chronic Wound Fluid." Wound Repair and Regeneration. Miami, 1993. pp. 181-186.
Chariker, M.E., et al, "Effective Management of Incisional and Cutaneous Fistulae with Closed Suction Wound Drainage," Contemporary Surgery. Jun. 1989, pp. 59-63, vol. 34.
Edlich, R.F., et al.: "Evaluation of a New, Improved Surgical Drainage System," The American Journal of Surgery, vol. 149, pp. 295-298, Feb. 1985.
Garcia-Rinaldi, R., et al., Improving the Efficiency of Wound Drainage Catheters, Amer. Journ. of Surg., Sep. 1975, 130, 372-373.
Gorica Zivadinovic, et al., "Vacuum Therapy in the Treatment of Peripheral Blood Vessels," Conference Papers of the 5th Timok Medical Days, Majdanpek, 1986 (161-164).
Health Technology, Literature R., "Vacuum Assisted Closure Therapy for Wound Care", Health Technology Literature Review (Dec. 2004), 3-59.
Jeter, Katherine F., et al., "Managing Draining Wounds and Fistulae: New and Established Methods", Chronic Wound Care, 1990, pp. 240-246.
McLaughlan, James, Sterile Microenvironment for Postoperative Wound Care, The Lancet, pp. 503-504, Sep. 2, 1978.
Meyer, MD., et al., "In Surgery, Medicine and the Specialties a Manual of its Practical Application", Bier's Hyperemic Treatment, Second Revised Edition, W.B. Saunders Company, 1909.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Mulder, GD, et al., "Clinicians' Pocket Guide to Chronic Wound Repair," Wound Healing Publications Second Edition, 1991.
Renasys EZ System for Negative Wound Therapy, Smith & Nephew announcement, dated Feb. 24, 2009, in 3 pages.

(56) References Cited

OTHER PUBLICATIONS

Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (322-326).
Sames, C.P., Sealing of Wounds with Vacuum Drainage, Br. Med. Journ., Nov. 5, 1977, p. 1223, Correspondence.
Sandén, Göran MD., et al., "Staphylococcal Wound Infection in the Pig: Part II. Inoculation, Quantification of Bacteria, and Reproducibility," Annals of Plastic Surgery, vol. 23, No. 3, Sep. 1989, (219-223).
Smith & Nephew, "PICO Single Use Negative Pressure Wound Therapy System", spiral booklet, Mar. 2011, in 7 pages.
Stewart, Joanne, Ph.D., World Wide Wounds—Next generation of products for wound management—2002 (13 pages).
Svedman, et al., "Staphylococcal Wound Infection in the Pig: Part I. Course," Annals of Plastic Surgery, vol. 23, No. 3, Sep. 1989 (212-218).
Tribble, David E. M.D., An Improved Sump Drain-Irrigation Device of Simple Construction, Archives of Surgery New York, pp. 511-513, 1972 vol. 105.
Usupov, et al., "Active Wound Drainage," Russian Journal: Vestnik Khirugii, Apr. 1987, (42-45).
Wu, W.S., et al. Vacuum therapy as an intermediate phase in wound closure: a clinical experience, Eur J Past Surg (2000) 23: 174-177.
Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.
Nullification of the German part of European patent 2 021 046 (German file references 60 2007 021 330.4), dated Nov. 23, 2015, with translation.
Notice of Appeal and subsequently filed items re EP 2254647, dated Oct. 25-27, 2017, in 6 pages.
Summons to attend oral proceedings and annex to the communication, dated Nov. 28, 2016, in 10 pages.
Reply of the patent proprietor to the notice(s) of opposition, Auxiliary request in opposition 3-6 re EP 2254647, dated Jul. 28, 2017, in 16 pages.
Annex to an opposition letter re EP 2254647, dated Jul. 27, 2017, in 6 pages.
Written submission in preparation to oral proceedings, letter accompanying subsequently filed items re EP 2254647, dated Sep. 15, 2017, in 5 pages.
Letter accompanying subsequently filed items and oral proceedings: reply to date proposed re EP 2254647, dated Sep. 27, 2017, in 3 pages.
Information about the result or oral proceedings re EP 2254647, dated Sep. 28, 2017, in 1 page.
Minutes of the oral proceedings, Decision of the Opposition Division, Decision rejecting the opposition, and Summary of facts and submissions re EP 2254647, dated Oct. 16, 2017, in 20 pages.
International Search Report and Written Opinion, re PCT Application No. PCT/US2009/037133, dated May 18, 2009.
International Preliminary Report on Patentability, re PCT Application No. PCT/US2009/037133, dated Sep. 23, 2010.
"Technology Watch", May 1989, in 1 page.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.

* cited by examiner

SHEAR RESISTANT WOUND DRESSING FOR USE IN VACUUM WOUND THERAPY

CROSS-REFERENCE TO RELATED APPLICATIONS

This application is a continuation application of U.S. application Ser. No. 14/948,024, filed on Nov. 20, 2015 and issued as U.S. Pat. No. 9,375,353 entitled "SHEAR RESISTANT WOUND DRESSING FOR USE IN VACUUM WOUND THERAPY", which is a continuation application of U.S. application Ser. No. 12/402,840, filed on Mar. 12, 2009 and issued as U.S. Pat. No. 9,199,012, which claims priority to, and the benefit of, under 35 U.S.C § 119(e), U.S. Provisional Application No. 61/036,275, filed on Mar. 13, 2008 by Vitaris, the entire contents of which are being hereby incorporated by reference herein in their entirety and are to be considered a part of this specification.

BACKGROUND

1. Technical Field

The present disclosure relates generally to a wound dressing for treating an open wound with a vacuum wound therapy procedure. In particular, the disclosure relates to a wound dressing employing a reticulated or net-like reinforcement structure to protect the wound throughout the procedure.

2. Background of Related Art

The body's natural wound healing process is a complex series of events beginning at the moment of injury. Initially the body reacts by delivering proteins and other factors to the wound through the blood stream to minimize the damage. Blood clots to prevent blood loss while cells engulf bacteria and debris to carry it away from the wound site. Next, the body begins to repair itself in a stage of healing often referred to as the proliferate phase. This phase is characterized by the deposition granulation tissue in the wound bed. Granulation tissue provides a base structure over which cells may migrate inwardly from the periphery to close the wound. Finally the process ends as collagen gives strength to new tissue over time often forming a scar.

One technique for promoting the natural healing process, particularly, but not exclusively during the proliferate phase, is known as vacuum wound therapy (VWT). Application of a reduced pressure, e.g. sub-atmospheric, to a localized reservoir over a wound has been found to assist in closing the wound. The reduced pressure may be effective to promote blood flow to the area, to stimulate the formation of granulation tissue and the migration of healthy tissue over the wound by the natural process. Also a reduced pressure may assist in removing fluids exuding from the wound, which may inhibit bacterial growth. This technique has proven effective for chronic or non-healing wounds, but has also been used in for other purposes such as post-operative wound care.

The general VWT protocol provides for the introduction of a filler material into the wound to absorb exudates and promote fluid transport away from the wound bed. The wound filler may comprise such materials as non-reticulated foams, non-woven reinforcements or gauze. The wound and the absorbent wound filler material may then be covered by a flexible cover layer having an adhesive periphery that forms a substantially fluid tight seal with the healthy skin surrounding the wound. The cover layer thus defines a vacuum reservoir over the wound where a reduced pressure may be maintained over time by individual or cyclic evacuation procedures.

An aspect of concern in a VWT treatment is the management of forces generated in the dressing when a reduced pressure is applied. These forces may undesirably deform a flexible cover layer, draw the peri-wound margins into the wound and put the surrounding skin in tension. These same forces may significantly compress the absorbent filler such that it forms a rigid mass. In such a state, the filler adopts an increased tendency to adhere to the wound bed, restricts the fluid passages available for exudate transport and inhibits penetration of the reduced pressure there through. Accordingly, a need exists for a dressing suitable for use in a VWT procedure.

SUMMARY

The present disclosure describes a dressing for use in a vacuum wound therapy procedure to promote healing of a wound. The dressing includes a cover layer having an integrated support structure to manage forces associated with a VWT procedure. The cover layer includes a backing layer formed from a flexible polymeric membrane, an adhesive layer to affix the backing layer over a wound and provide to a seal around the wound bed, and a reticulated or net-like reinforcement layer affixed to the backing layer and extending to a peripheral region of the cover layer. The net-like reinforcement layer stiffens the cover layer and contributes to the ability of the cover layer to resist the deformation in the wound area commonly associated with a VWT procedure. Thus, the wound filler may be compressed to a minor degree such that it continues to provide exudate transport and vacuum penetration. The use of the net-like reinforcement layer may also lessen the degree to which the wound margin collapses, and may contribute to the manifestation of forces generated by the application of a reduced pressure as compression forces rather than shear forces. Compression forces applied to a wound is well known to be a beneficial wound treatment.

The reinforcement layer may be formed from such structures as a mesh of polyethylene terephthalatae fibers, apertured films and thermoplastic netting. The adhesive layer may be affixed to a peripheral region of the backing layer and may include an opening such that the adhesive layer does not extend to a central region of the cover layer. The adhesive layer may overlap a portion of the reinforcement layer such that the reinforcement layer is firmly affixed to the backing layer. Alternatively, the reinforcement layer may contain an appropriate adhesive coating to more firmly attach it to the backing layer. The backing layer may be formed from a polyurethane film having a thickness from about 0.8 mils to about 1.0 mils, and may include an aperture therein for facilitating connection of a vacuum port to the cover layer. The vacuum port may incorporate a filter screen defining a plurality of openings. The backing layer may be formed from a moisture vapor permeable membrane.

According to another aspect of the disclosure a wound dressing system includes a contact layer and an absorbent filler positioned in a wound bed and covered by a cover layer. A vacuum reservoir is defined between the cover layer and the wound bed. The cover layer includes a backing layer formed from a flexible polymeric membrane, an adhesive layer to affix the backing layer over a wound and provide to a seal around the wound bed, and a reinforcement layer affixed to the backing layer and extending to a peripheral region of the cover layer. A vacuum system is in fluid communication with the vacuum reservoir.

The contact layer may be formed from a conical apertured film to promote unidirectional flow of exudates from the wound. The absorbent filler material may include a single strand of a polyolefin filament. Also, the vacuum system may include a vacuum source, a collection canister and a one-way valve.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

The wound dressing of the present disclosure promotes healing of a wound by providing a reservoir over the wound where a reduced pressure may be maintained. The reservoir subjects the wound to a sub-atmospheric pressure to effectively draw wound fluid, including liquid exudates, from the wound without the continuous use of a vacuum pump. Hence, vacuum pressure may be applied once, or in varying intervals depending on the nature and severity of the wound. To facilitate fluid transport from the wound, a filler material may be included within the reservoir to promote the wicking of wound fluids subject to a reduced pressure. The use of a wound dressing in this manner has been found to promote healing by reducing the probability of infection, stimulating the deposition of granulation tissue and other beneficial processes. The wound dressing of the present disclosure includes a cover layer having a reinforcement structure to enhance the effect of a vacuum wound therapy treatment.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

Figure 1:
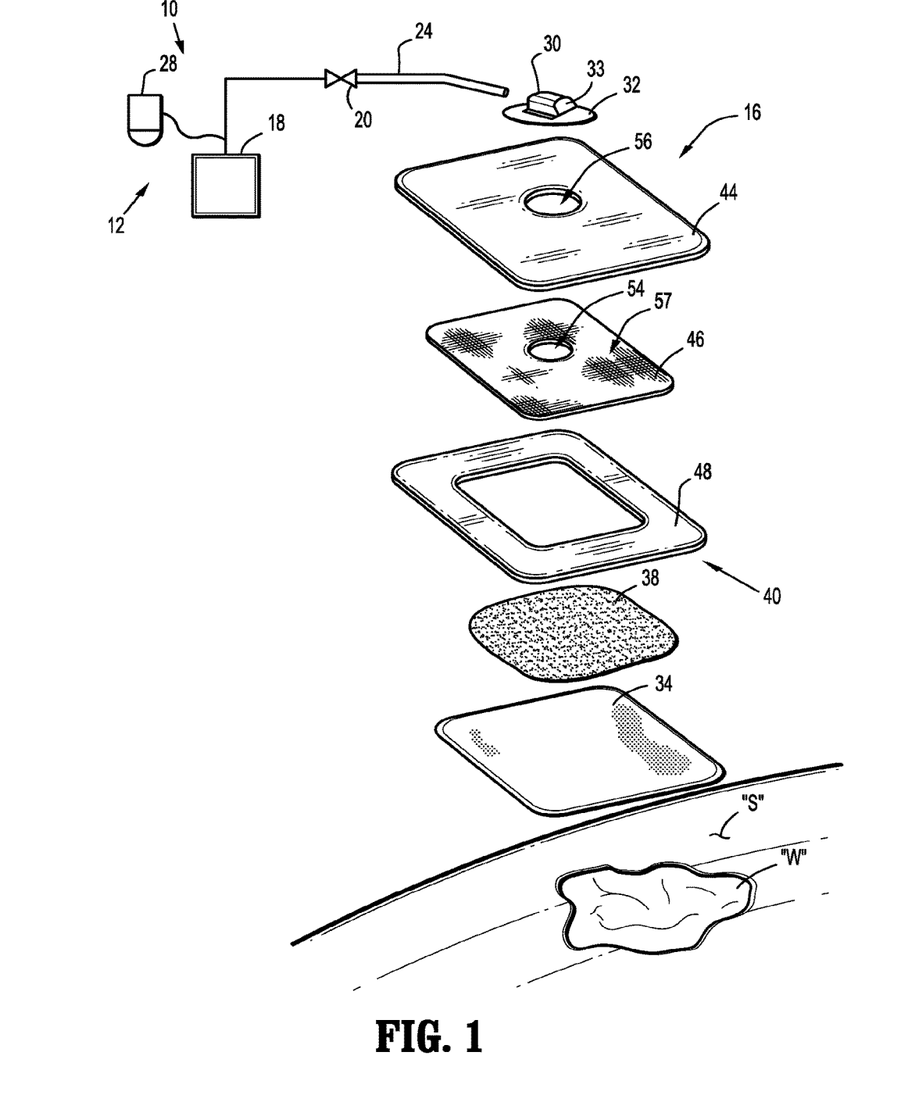
FIG. 1 is an exploded perspective view of a vacuum wound therapy system in accordance with the present disclosure.

Referring initially to FIG. 1, a vacuum wound therapy system according to the present disclosure is depicted generally as 10 for use on a wound "w" surrounded by healthy skin "s." The vacuum wound therapy system 10 includes a vacuum system 12 in fluid communication with a vacuum reservoir 14 (FIG. 4A) defined by or within wound dressing 16. The vacuum system 12 includes a vacuum source 18 coupled to the dressing 16 through a one-way valve 20 and a vacuum tube 24. A collection canister 28 may be provided for wound drainage and debris. The vacuum system 12 is adapted to provide a reduced pressure to the vacuum reservoir 14 appropriate to stimulate healing of the wound "w." A more detailed description of an appropriate vacuum system 12 is found in commonly assigned U.S. Patent Application Publication 2007/0066946, the entire contents of which are incorporated herein by reference.

Figure 5:
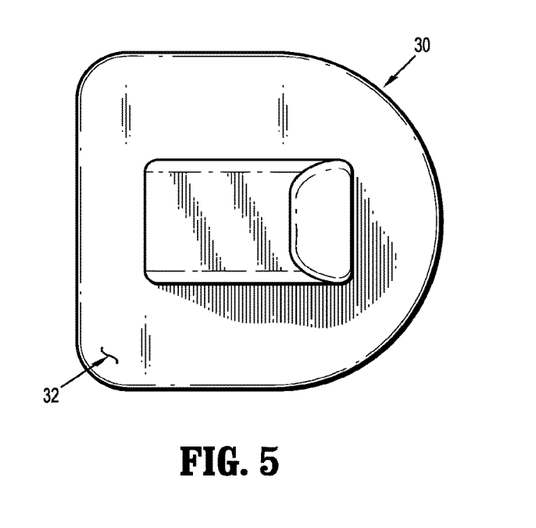
FIG. 5 is a top plan view of a vacuum port of FIG. 1.
Figure 6:
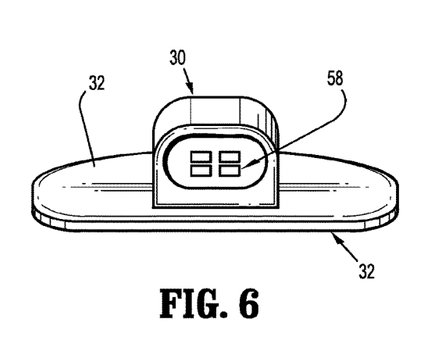
FIG. 6 is a perspective view of the vacuum port of FIG. 5.
Figure 7:
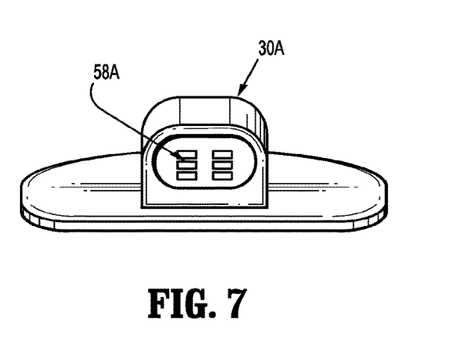
FIG. 7 is a perspective view of an alternative embodiment of a vacuum port.

A vacuum port 30, depicted in greater detail in FIG. 5 and FIG. 6, may also be included to facilitate connection of the vacuum system 12 to the dressing 16. The vacuum port 30 may be configured as a rigid or semi-rigid, low-profile component adapted to receive the vacuum tube 24 in a releasable and fluid-tight manner. The vacuum port 30 may be configured to include a wide and flexible flange 32 about its perimeter. The flange 32 permits an adhesive to be attached to either an underside of flange 32 for securement to an outer surface of cover layer 44, or to a top side of flange 32 to provide for mounting to the underside of the reinforcement layer 46. Either configuration provides a mechanism for connecting to the dressing 16. A hollow interior of the vacuum port 30 provides fluid communication between the vacuum tube 24 and the reservoir 14 defined by or within dressing 16. A connector segment 33 extends above the flange 32 for facilitating connection with the vacuum tube 24. It is envisioned that because of the possible intimate proximity of the vacuum port 30 to either reservoir 14 or wound filler 38, the performance of vacuum port 30 may be enhanced by the incorporation of a filter screen 58 as depicted in FIG. 6 and FIG. 7. Filter screen 58 may inhibit the migration of large particles that may otherwise be drawn into the vacuum port 30 and consequently create a restriction or blockage of the vacuum tube 24. The filter screen 58 may be integral to the configuration of the vacuum port 30 as part of the port flange 32. The filter screen 58 may include a number of openings, each smaller than a cross-sectional area of the vacuum tube 24 or the opening in the vacuum port 30 adapted to receive the vacuum tube 24, and collectively greater than the cross-sectional area of vacuum tube 24 or the opening in the vacuum port 30 adapted to receive the vacuum tube 24. For example, the filter screen 58 of vacuum port 30 may include four relatively large openings, while the filter screen 58A of vacuum port 30A depicted in FIG. 7 may include six relatively small openings. The openings in the filter screens 58, 58A are dimensioned to minimize the passage of tissue particles of a predetermined dimension through the respective vacuum port 30, 30A.

Figure 8:
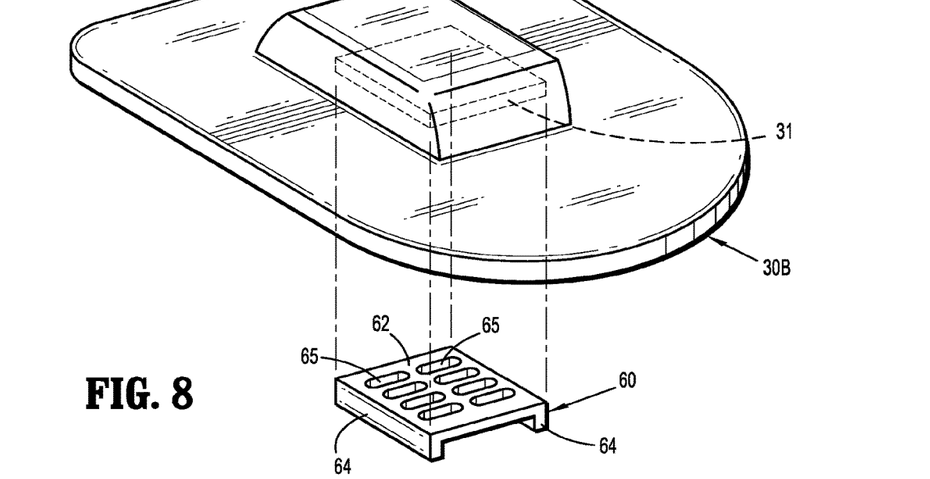
FIG. 8 is an exploded perspective view of an alternative embodiment of a vacuum port assembly including a portal member and an independent filter screen.
Figure 8A:
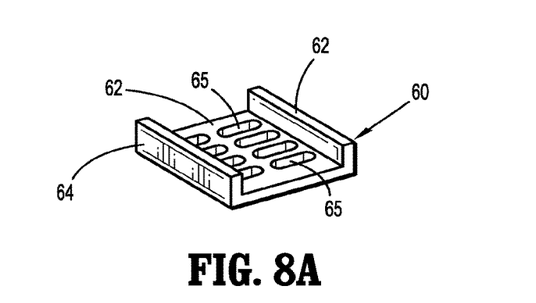
FIG. 8A is a perspective view of the filter screen of FIG. 8 in an alternate orientation.
Figure 8B:
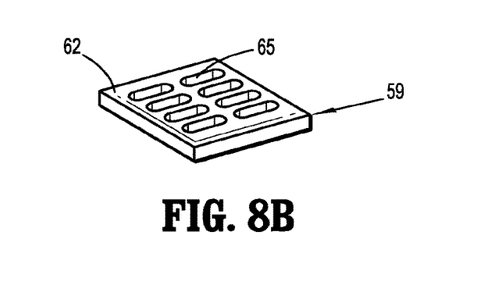
FIG. 8B is a perspective view of an alternate embodiment of an independent filter screen.
Figure 9:
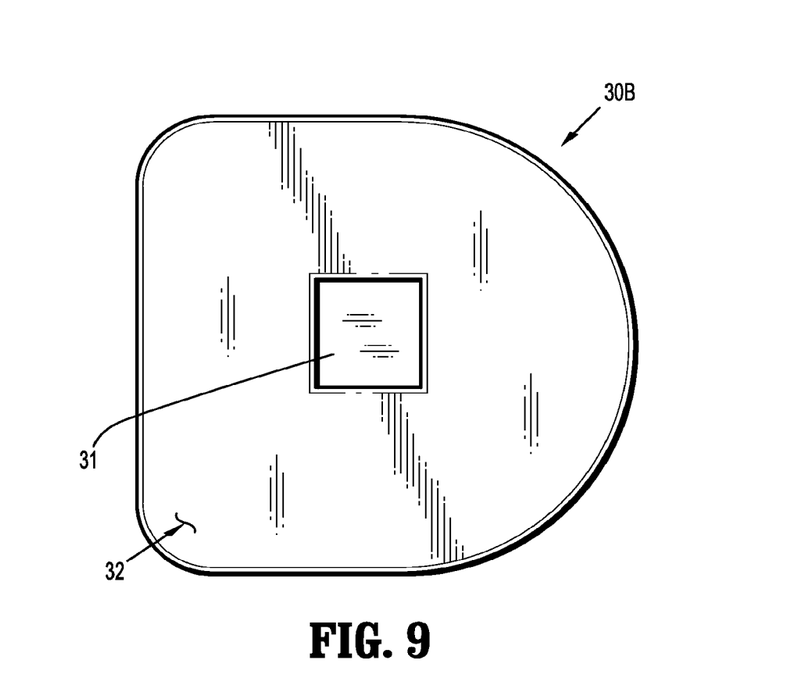
FIG. 9 is a bottom plan view of the portal member of FIG. 8.
Figure 10:
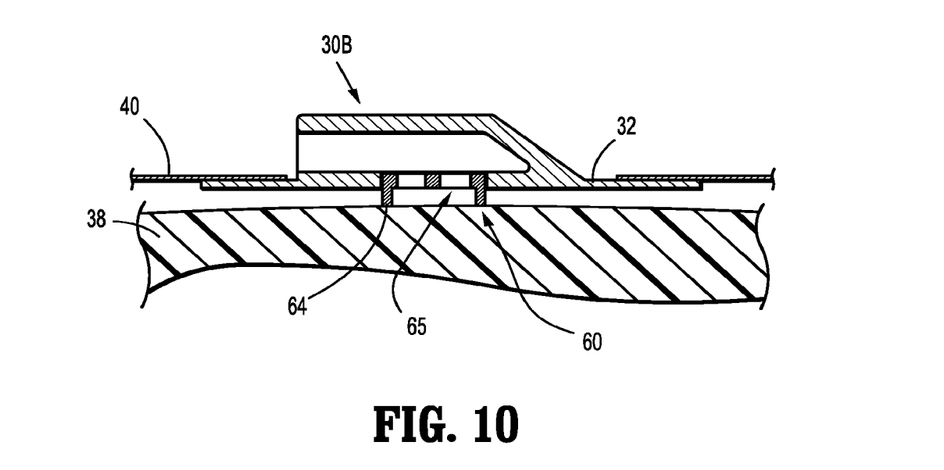
FIG. 10 is a partial cross sectional view of the vacuum port assembly assembled in a wound dressing.
Figure 11:
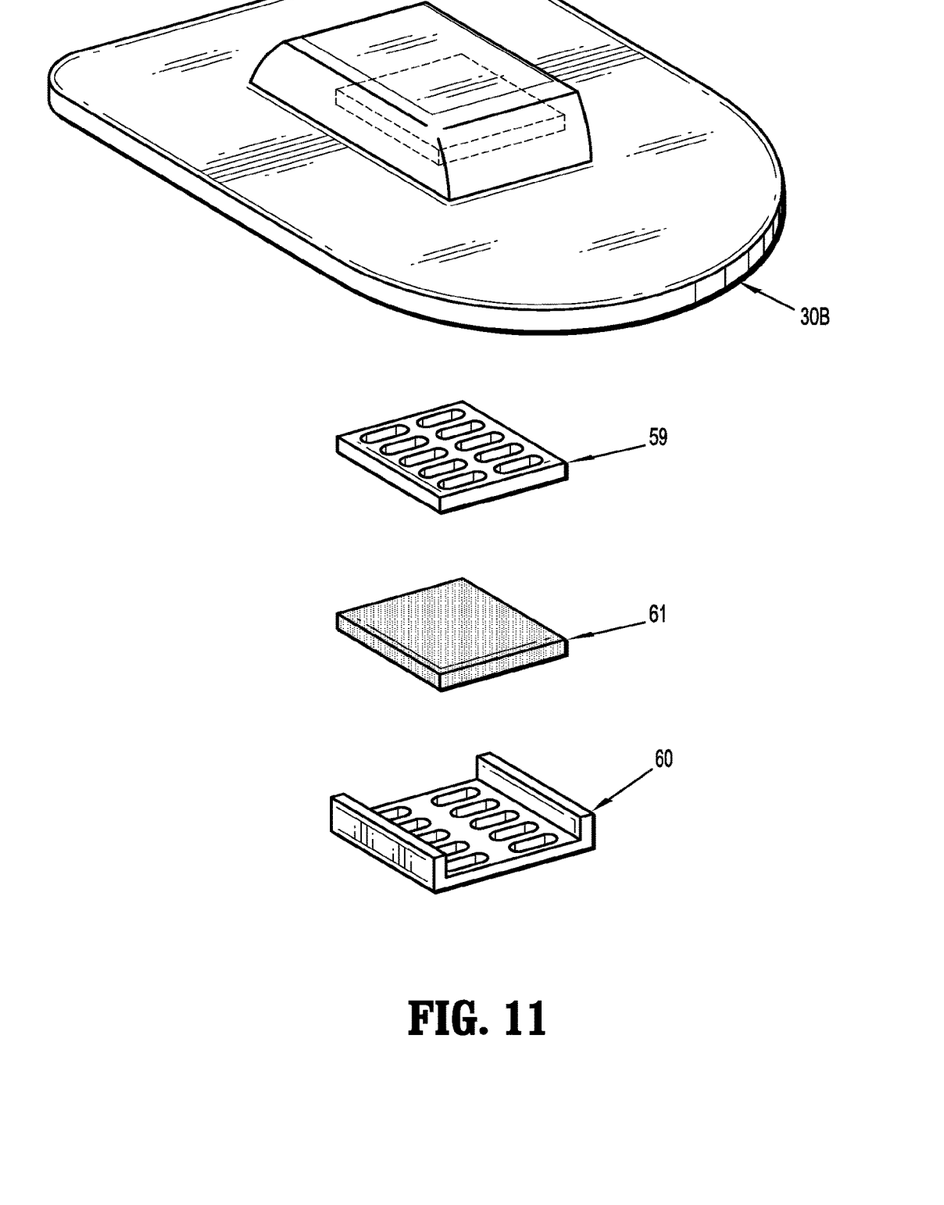
FIG. 11 is an exploded perspective view of an alternative embodiment of a vacuum port assembly including a treatment element.

Another alternate embodiment of a vacuum port is depicted generally as 30B in FIGS. 8, 9, 10 and 11. Vacuum port 30B may be configured to accept a filter screen 59 or 60 as a distinct or independently manufactured component as depicted in FIGS. 8, 10 and 11. An opening or cavity 31 depicted in the plan view of FIG. 9 and shown in phantom in FIG. 8 on an underside of vacuum port 30B may be adapted to permit filter screen 59 to be permanently bonded therein such that filter screen 59 is substantially flush with the underside of vacuum port 30B. Alternatively, filter screen 60 may be bonded to the opening on the underside of vacuum port 30B. Filter screen may 60 includes a generally flat base 62 through which the openings 65 extend, and a pair lips 64 projecting from the base 62 along opposite edges of the filter screen 60. The lips 64 may be dimensioned to be flush with a patient facing under surface of the flange when received within the cavity 31. Alternatively the lips 64 may extend beyond the under surface of the flange to extend beyond the cavity 31 in the portal member 30B as depicted in FIG. 10. Filter screen 60 may exhibit an increased surface area available for bonding within cavity 31 of vacuum port 30B. Filter screen 60 may be secured within cavity 31 by bonding, cements, adhesives or the like. In one embodiment, filter screen 62 is positioned within cavity 31 with lips 64 facing toward the wound (FIGS. 8 and 10). In another embodiment, filter screen 62 is positioned within lips 64 facing toward vacuum port 30B and away from the wound (FIG. 8A). In another embodiment, base 62 is devoid of lips 64 as shown in FIG. 8B, and is substantially planar.

It is also envisioned that filter screens 59 and 60 may be provided in combination with a treatment element 61 comprising a therapeutic material as depicted in FIG. 11. Treatment element 61 may be inserted between filter screens 59, 60 and may secured to vacuum port 30B by an appropriate adhesive bond. The treatment element 61 and filter screens 59, 60 may define an insert for reception into cavity or opening 31 on the underside of portal member 30B. This arrangement may provide a convenient method of treating the wound exudate as it is drawn from the wound "w." Treatment element 61 may comprise fibrous or granulated materials contained in a porous container or wrap to facilitate placement between filter screens 59 and 60. Treatment element 61 may include materials such as activated charcoal or other odor control or neutralizing substances. Treatment element 61 may include anti-bacterials such as polyhexamethylene biguanide (PHMB). Also, antimicrobials such as ionic metals or biguinides may be included to reduce the bio-burden of the exudate or microbials within the exudate as the exudate is drawn in to a collection canister 28. In the alternative, filter screens 59, 60 may comprise charcoal, antimicrobials, anti-odor substances.

Vacuum tube 30 may be configured to accept a variety of tubing geometries such as round, oblong or elliptical. Vacuum port 30 may be provided as a pre-affixed component of dressing 16, as part of vacuum system 12 or entirely independently. Also vacuum port 30 may not be necessary depending on the configuration of dressing 16.

Wound dressing 16 generally includes a contact layer 34, filler 38 and a reinforced cover layer 40. Reinforced cover layer 40 may be formed from a composite including a backing layer 44, a reinforcement layer 46 and an adhesive layer 48. Each layer of wound dressing 16 is described in greater detail below.

Contact layer 34 may be sufficiently conformable to be positioned in direct contact with an irregularly shaped surface of a wound bed "w." A thin film of polyethylene or other suitable non-adherent material may form the contact layer 34 to limit the adherence of filler 38 and other substances to the wound "w." Apertures or perforations in the film permit fluids to pass through the contact layer 34, allowing for the sub-atmospheric pressure to penetrate into the wound "w" and for exudates to flow freely out of the wound "w." By selecting an appropriate film material, the passage of wound exudate through contact layer 34 may be controlled so as to be substantially unidirectional to prevent wound exudate from flowing back into the wound. To promote a unidirectional flow, a conical apertured film, such as those provided by Tredegar Film Products of Richmond, Va., may be selected for forming contact layer 34. This type of film is arranged with apertures positioned at the peaks of cone shaped formations in the film material such that exudate encounters the film as an array of micro-funnels in one direction and an array of collecting basins in the other. Though it is depicted in a square configuration, the shape of the contact layer 34 can be customized to better suit the wound geometry. Unidirectional flow of exudates may also be promoted by the selection of other materials including a lamination of layers having varying absorptive characteristics. One exemplary material, which may be used as a contact layer is sold under the trademark XEROFLO® by Kendall Corp., a division of Covidien.

Figure 4A:
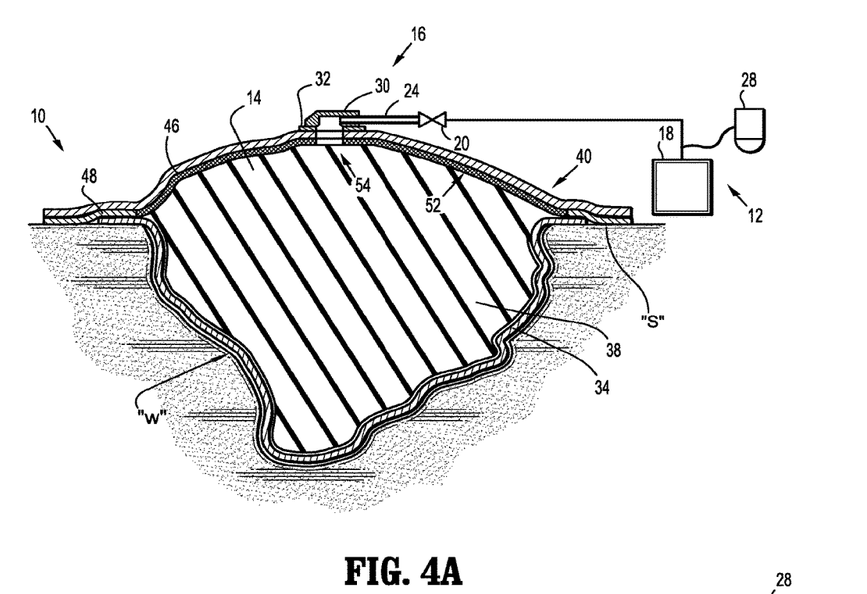
FIG. 4A is a cross sectional view of the vacuum wound therapy system of FIG. 1 installed over wound on a patient prior to application of a reduced pressure.

Filler 38 may be arranged over contact layer 34 to fill wound "w" to the level of the surrounding healthy skin "s" or may over-fill the wound "w" as depicted in FIG. 4A. An absorbent material such as non-woven gauze or reticulated foam may be used for filler 38 to trap or transport any exudate that migrates through contact layer 34. An antimicrobial dressing sold under the trademark KERLIX® by Kendall Corp., a division of Covidien, may be suitable for use as filler 38. To prevent adhesion to the wound "w," the filler 38 may also comprise a material configured such that any stray fibers do not tend to protrude through apertures of contact layer 34 where they may become engulfed by newly forming granulation tissue. One particular type of material exhibiting this characteristic is often referred to as "tow." The manufacturing process for synthetic fibers often includes an extrusion of an indeterminate length of continuous filaments, which are spun together to form fibers. It is the continuous lengths of un-spun filaments which are referred to as tow. A single length of tow formed from a hydrophobic material such as polyolefin may be laid in the wound bed "w" to form filler 38. This arrangement allows for a complete removal of filler 38 when the dressing 16 is changed without re-injuring the wound "w."

Figure 2:
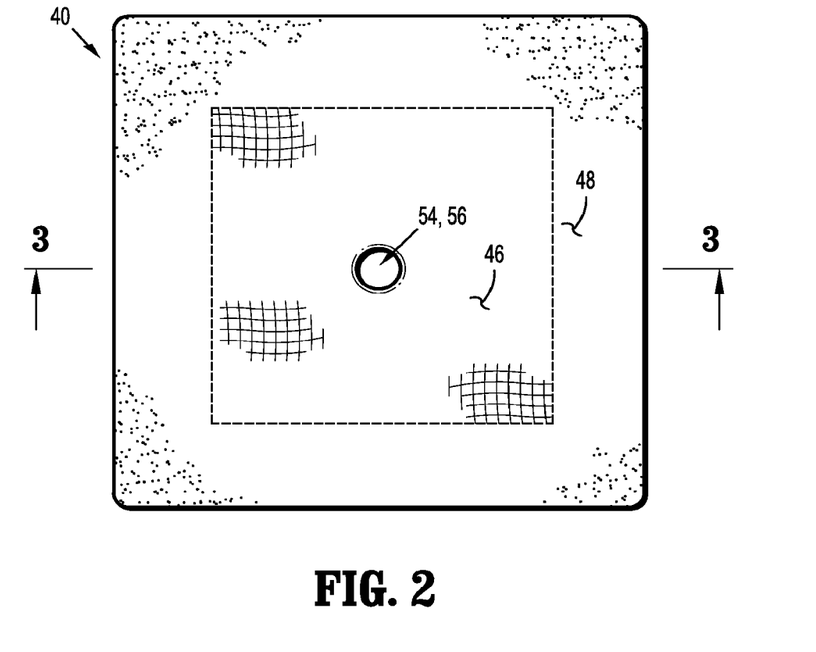
FIG. 2 is an orthographic view of a wound facing side of the cover layer of FIG. 1.

Cover layer 40 may be placed over the wound "w" enclosing the contact layer 34 and filler 38 therein. The periphery of cover layer 40 extends laterally beyond the perimeter of the wound bed "w" so as to contact the healthy skin "s" to form a seal over the wound "w." As depicted in FIG. 2, adhesive layer 48 may extend to the periphery of cover layer 40 to provide the seal with the use of a medical-grade, pressure-sensitive adhesive. The adhesive layer 48 may be adapted to provide a fluid-tight and bacteria-tight seal around a peripheral region of dressing 16 such that exudate cannot escape through the edges of the dressing 16 and external air and contaminants may not enter the wound area. To provide such a barrier, the adhesive layer 48 may, for example, be on the order of 1.0 to 10 mils thick depending on the adhesive used. In general, a high peal-strength adhesive may be used to resist inadvertent lift-off, roll or "flagging," i.e., a failure of the dressing to adhere to itself or the patient, at the edges of the cover layer 40. The adhesive defining the adhesive layer 48 may include, but is not limited to, medical grade acrylics, rubber base or silicone adhesives. Preferably, those adhesives included with the dressing sold under the trademark Polyskin II Transparent Dressings by Kendall Corp., a division of Covidien, may be used. Adhesive layer 48 forms a continuous band around the peripheral region of cover layer 40, but contains an opening such that the adhesive layer does not extend inwardly to the central areas of cover layer 40.

Figure 3:
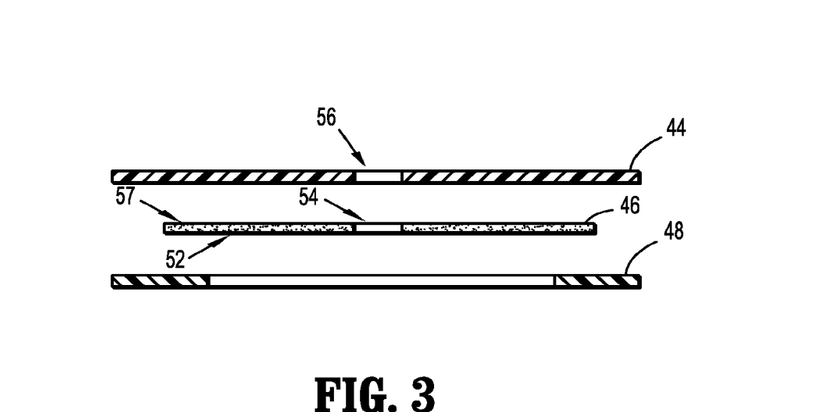
FIG. 3 is an exploded cross sectional view taken along the line 3-3 of FIG. 2.

As depicted in FIG. 3, reinforcement layer 46 may overlap adhesive layer 48 at an outer edge such that an outer periphery of reinforcement layer 46 is firmly affixed to backing layer 44. Reinforcement layer 46 extends to a peripheral region of cover layer 40, but not necessarily to an outer perimeter of the cover layer 40. Reinforcement layer 46, particularly any portion not overlapping the adhesive layer 48, may be affixed to backing layer 44 with a light coat of an adhesive 57 applied to the appropriate side of the reinforcement layer 46 or the backing layer 44. A portion of a wound facing side 52 of the reinforcement layer 46 carries no adhesive to prevent adhesion of the cover layer 40 to the filler 38. An aperture 54 extends through the reinforcement layer 46 to permit fluid communication between the reservoir 14 and vacuum system 12.

The reinforcement layer 46 may comprise a mesh of polyethylene terephtalate (PET) fibers, which offer good liquid resistance making it suitable for use in a moist wound environment. PET fibers may be used to form woven or non-woven reinforcements having large pore sizes. Some PET reinforcement manufacturing methods provide for interlinking the fiber junctions to yield a mesh that is flexible in multiple directions and also does not unravel when cut. One such method is known as hydro-entanglement. PET reinforcements thus manufactured tend to have a high shear stiffness that may be useful in reinforcing cover layer 40. One exemplary material, which may be suitable for incorporation into reinforcement layer 46, is sold under the trademark Sontara® by DuPont. Alternatively, reinforcement layer 46 may be formed from another reinforcement or mesh structure having suitable shear stiffness. Examples of suitable structures include extruded netting and apertured films. Suitable materials for use in such alternate structures include PET, polyethylene, nylon and polypropylene. Additionally, woven structures may be used for reinforcement layer 46. Acceptable woven materials may include cotton gauze, woven acetate and nylon.

Extending to the periphery of the cover layer 40 is backing layer 44. Backing layer 44 provides a substrate to which reinforcement layer 46 and adhesive layer 48 may be affixed. An aperture 56 extends through the backing layer 44 to permit fluid communication between the reservoir 14 and vacuum system 12. Backing layer 44 may be formed from a flexible polymeric membrane to serve as a fluid barrier to allow for a sub-atmospheric pressure to be established in vacuum reservoir 14, and also as a microbial barrier preventing contaminants from entering the wound area. For example, backing layer 44 may comprise a polyurethane film having a thickness from about 0.8 mils to about 1.0 mil. Preferably, the backing layer 44 is formed from a moisture vapor permeable membrane to promote the exchange of oxygen and moisture vapor between the wound site and the atmosphere. One exemplary material is a transparent membrane sold under the trade name POLYSKIN® II by Kendall Corp., a division of Covidien. Other materials which may be suitable for use in a backing layer include the thin films marketed under the names TEGADERM™ by 3M of St. Paul, Minn. and OPSITE™ by Smith and Nephew PLC of London, UK. Reinforcement layer 46 may be configured so as not to impede the transmission of moisture vapor by including, for example, a large pore size.

Figure 4B:
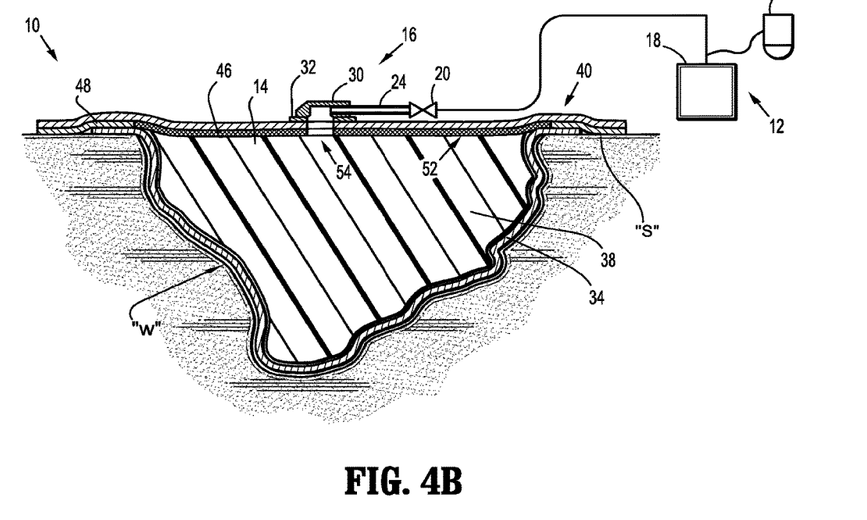
FIG. 4B is a cross sectional view of the vacuum wound therapy system of FIG. 1 installed over wound on a patient following an application of a reduced pressure.

As seen in FIG. 4A, reservoir 14 is defined by or within wound dressing 16 when applied to the skin Filler 38 may be included to fill the reservoir 14. Evacuating atmospheric gasses from the reservoir 14 may impart a tendency for cover layer 40 to flatten against the wound "w" as depicted in FIG. 4B. This tendency of cover layer 40 to deform may draw the peri-wound margins into the wound "w" and put the surrounding skin "s" in tension. This tendency may be counteracted or resisted by the shear stiffness in reinforcement layer 46 such that the cover layer 40 may better maintain its shape. Because reinforcement layer 46 extends to a peripheral region of cover layer 40 and backing layer 44 anchored to healthy skin "s," the forces associated with evacuating reservoir 14 may be transferred beyond the perimeter of the wound "w," and may be manifested as compression forces. Thus reinforcement layer 46 reinforces cover layer 40 and vacuum reservoir 14.

A central region of reinforcement layer 46 may be devoid of an adhesive coating, such that the reinforcement layer 46 may not tend to adhere to or disturb filler 38, particularly as the reduced pressure is removed from reservoir 14. Reinforcement layer 46 thus further protects wound "w" to promote healing throughout the evacuation cycles of a VWT procedure.

Although the foregoing disclosure has been described in some detail by way of illustration and example, for purposes of clarity or understanding, it will be obvious that certain changes and modifications may be practiced within the scope of the appended claims.

What is claimed is:

1. A negative pressure wound therapy dressing comprising:
   a backing layer comprising a flexible polymeric membrane, the backing layer including a lower wound facing side, an upper side opposite the lower wound facing side, and an aperture extending through the backing layer;
   a porous layer disposed below the lower wound facing side of the backing layer;
   an absorbent filler, wherein the absorbent filler is configured to be in fluid communication with the porous layer and configured to collect exudate removed from a wound; and
   a vacuum port configured to be fluidically connected, via a tube, to a negative pressure source, wherein the vacuum port comprises:
      a flange having an underside and a top side, wherein the underside of the flange has an opening positioned over the aperture in the backing layer and the underside of the flange is positioned on the upper side of the backing layer; and
      a connector extending above the flange, the connector configured to be connected to the tube;
   a screen positioned across the opening on the underside of the flange configured to prevent migration of particles into the vacuum port, wherein the screen comprises openings having a size configured to prevent migration of particles into the vacuum port, the size of the openings being large enough for liquid wound exudate to pass through the screen.

2. The dressing according to claim 1, wherein the porous layer is substantially liquid resistant.

3. The dressing according to claim 1, wherein the porous layer comprises a reticulated material.

4. The dressing according to claim 1, wherein the porous layer comprises a network of interlinked fibers that comprises a mesh formed from polyethylene terephthalate fibers (PET).

5. The dressing according to claim 1, wherein the connector comprises a connector segment extending above the flange, wherein the connector segment extends radially outward parallel to a base of the flange and is configured to receive the tube.

6. The dressing according to claim 1, further comprising an adhesive disposed on the lower wound facing side of the backing layer, wherein the adhesive is affixed to a peripheral region of the backing layer and includes an opening such that the adhesive does not extend to a central region of the dressing.

7. The dressing according to claim 6, wherein the adhesive overlaps a portion of the porous layer such that the porous layer is affixed to the backing layer.

8. The dressing according to claim 1, wherein the backing layer comprises a polyurethane film having a thickness from about 0.8 mils to about 1.0 mils.

9. The dressing according to claim 1, wherein the backing layer comprises a moisture vapor permeable membrane.

10. The dressing according to claim 1, wherein the absorbent filler comprises material configured to trap exudate.

11. The dressing according to claim 1, in combination with the negative pressure source configured to provide reduced pressure to the wound.

12. The dressing according to claim 1, further comprising a wound contact layer configured to be in direct contact with the wound, wherein the absorbent filler is configured to be positioned over the wound contact layer; wherein the wound contact layer is configured to promote a substantially unidirectional flow of fluid so as to prevent exudate removed from the wound from flowing back into the wound when vacuum is applied to the wound.

13. The dressing according to claim 12, wherein the backing layer, the porous layer and the wound contact layer have a square shape.

14. The dressing according to claim 1, wherein the aperture in the backing layer is located in a central region of the backing layer.

15. The dressing according to claim 1, wherein the porous layer comprises an aperture that extends through the porous layer to permit fluid communication between the wound and the negative pressure source.

16. The dressing according to claim 1, wherein the vacuum port comprises a cavity on an underside of the vacuum port, wherein the screen is positioned within the cavity.

17. The dressing according to claim 16, wherein the screen is substantially flush with the underside of the flange.

18. The dressing according to claim 1, further comprising a one-way valve positioned between the vacuum port and the negative pressure source.

19. The dressing according to claim 18, wherein the one-way valve is positioned at an end of the tube located away from the backing layer and toward the negative pressure source.

20. The dressing according to claim 1, wherein the screen comprises a filter configured to minimize particles of predetermined dimension from passing through the screen.

* * * * *